US006992204B2

(12) United States Patent
Damrau et al.

(10) Patent No.: US 6,992,204 B2
(45) Date of Patent: Jan. 31, 2006

(54) METHOD FOR THE SELECTIVE PRODUCTION OF RACEMIC METALLOCENE COMPLEXES

(75) Inventors: Robert Damrau, Constance (DE);
Patrik Müller, Kaiserslautern (DE);
Eva Royo, Constance (DE);
Hans-Herbert Brintzinger, Tägerwilen (CH)

(73) Assignee: Basell Polyolefine GmbH, Frankfurt am Main (DE)

( * ) Notice: Subject to any disclaimer, the term of this patent is extended or adjusted under 35 U.S.C. 154(b) by 50 days.

(21) Appl. No.: 10/312,359

(22) PCT Filed: Jun. 28, 2001

(86) PCT No.: PCT/EP01/07389

§ 371 (c)(1),
(2), (4) Date: Jun. 5, 2003

(87) PCT Pub. No.: WO02/00672

PCT Pub. Date: Jan. 3, 2002

(65) Prior Publication Data

US 2004/0010157 A1    Jan. 15, 2004

(51) Int. Cl.
*C07F 17/00* (2006.01)
*B01J 31/00* (2006.01)
*C08F 4/44* (2006.01)

(52) U.S. Cl. .............................. 556/53; 556/1; 556/11; 556/12; 556/43; 556/58; 526/126; 526/160; 526/943; 502/103; 502/117; 502/153

(58) Field of Classification Search .............. 556/1, 556/11, 12, 43, 53, 58; 502/103, 117, 153, 502/126, 160, 943
See application file for complete search history.

(56) References Cited

U.S. PATENT DOCUMENTS 6,262,286 B1    7/2001    Gregorius et al. ............ 556/11

FOREIGN PATENT DOCUMENTS

| EP | 700935 | 3/1996 |
|---|---|---|
| EP | 970964 | 1/2000 |
| WO | 92/09545 | 6/1992 |
| WO | 95/02567 | 1/1995 |
| WO | 99/15538 | 4/1999 |

OTHER PUBLICATIONS

Waymouth et al., *J.Am.Chem.Soc.*, 1990, v. 112, 4911-4914.
Kaminsky et al., *Angew,Chem.*, 101:9 (1989) 1304-06.
Coates et al., *J.Am.Chem.Soc.*, 1991, v. 113, 6270-6271.
Rheingold et al., *Organometallics*, 1992, v. 11, 1869-1876.
Van Der Linden et al., *J.Am.Chem.Soc.*, 1995, v. 117, 3008-21.
Yasuda et al., *J.Org.Chem.*, 1994, v. 473, 105-116.
Engelhardt et al., *J. Chem. Soc. Dalton Trans.*, 1987, 2347-2357.
Huttenloch et al. *J.Org.Chem.*, 1997, v. 541, 219-232.
Schmidt et al. *Organometallics*, 1997, v. 16, 1724-28.
Willoughby et al., *J.Am.Chem.Soc.*, 1994, v. 116, 11703-14.
Heron et al., *J.Am.Chem.Soc.*, 1997, v. 119, 6205-6.
Xu et al. *J.Am.Chem.Soc.*, 1997, v. 119, 10302-16.
Xin et al., *Can.J.Chem.*, 1995, v. 73, 999-1002.

*Primary Examiner*—Porfirio Nazario-Gonzalez
(74) *Attorney, Agent, or Firm*—Novak Druce & Quigg

(57) ABSTRACT

The invention relates to a method for producing racemic metallocene complexes by reacting bridged or non-bridged transition metal complexes with cyclopentadienyl derivatives of alkaline or alkaline earth metals and optionally, subsequently substituting the phenolate ligands.

11 Claims, No Drawings

METHOD FOR THE SELECTIVE PRODUCTION OF RACEMIC METALLOCENE COMPLEXES

The present invention relates to a process for preparing racemic metallocene complexes by reacting bridged or unbridged transition metal-aromatic complexes of the formula I

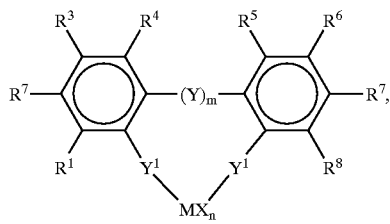

where the substituents and indices have the following meanings:

M is titanium, zirconium, hafnium, vanadium, niobium, tantalum, chromium, molybdenum, tungsten or an element of transition group III of the Periodic Table or a lanthanide, X are identical or different and are each fluorine, chlorine, bromine, iodine, hydrogen, $C_1$–$C_{10}$-alkyl, $C_6$–$C_{15}$-aryl, alkylaryl having from 1 to 10 carbon atoms in the alkyl part and from 6 to 20 carbon atoms in the aryl part, —$OR^{10}$ or —$NR^{10}R^{11}$, n is an integer from 1 to 4, where n corresponds to the valence of M minus 2, $R^1$, $R^8$ are identical or different and are each hydrogen, fluorine, chlorine, bromine, iodine, $C_1$–$C_{20}$-alkyl, 3- to 8-membered cycloalkyl which may in turn bear a $C_1$–$C_{10}$-alkyl group as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $Si(R^9)_3$ where $R^9$ are identical or different and are each $C_1$–$C_{20}$-alkyl, $C_3$–$C_{10}$-cycloalkyl, $C_6$–$C_{15}$-aryl, where the radicals mentioned may be partially or fully substituted by heteroatoms, —$OR^{27}$, —$SR^{27}$, —$N(R^{27})_2$, —$P(R^{27})_2$, where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$-alkyl, $C_6$–$C_{15}$-aryl, $C_3$–$C_{10}$-cycloalkyl, alkylaryl $R^2$ to $R^7$ are identical or different and are each hydrogen, $C_1$–$C_{20}$-alkyl, 3- to 8-membered cycloalkyl which may in turn bear a $C_1$–$C_{10}$-alkyl radical as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $Si(R^9)_3$ where $R^9$ are identical or different and are each $C_1$–$C_{20}$-alkyl, $C_3$–$C_{10}$-cycloalkyl, $C_6$–$C_{15}$-aryl, where adjacent radicals $R^2$ to $R^7$ may form saturated, partially saturated or unsaturated cyclic groups having from 4 to 15 carbon atoms, and the radicals mentioned may be fully or partially substituted by heteroatoms, —$OR^{27}$, —$SR^{27}$, —$N(R^{27})_2$, —$P(R^{27})_2$, where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$-alkyl, $C_6$–$C_{15}$-aryl, $C_3$–$C_{10}$-cycloalkyl, alkylaryl $R^{10}$, $R^{11}$ are each $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical, Y, $Y^1$ are identical or different and are each

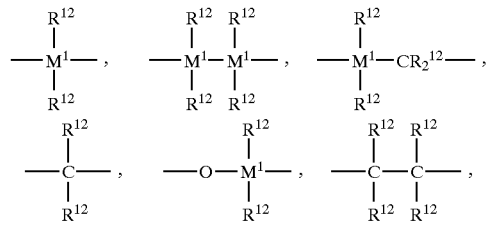

=$BR^{12}$, =$AlR^{12}$, —Ge—, —Sn—, —O—, —S—, =SO, =$SO_2$, =$NR^{12}$, =CO, =$PR^{12}$ or =$P(O)R^{12}$, where $R^{12}$ are identical or different and are each hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl, $C_7$–$C_{40}$-alkylaryl, or two radicals $R^{12}$ together with the atoms connecting them form a ring, $M^1$ is silicon, germanium or tin and m is 0, 1, 2, 3, or Y is nonbridging and represents two radicals R' and R", where R' and R" are identical or different and are each hydrogen, fluorine, chlorine, bromine, iodine, $C_1$–$C_{20}$-alkyl, 3- to 8-membered cycloalkyl which may in turn bear a $C_1$–$C_{10}$-alkyl group as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $Si(R^9)_3$ where $R^9$ are identical or different and are each $C_1$–$C_{20}$-alkyl, $C_3$–$C_{10}$-cycloalkyl, $C_6$–$C_{15}$-aryl or together with adjacent radicals $R^4$ or $R^5$ form saturated, partially saturated or unsaturated cyclic groups having from 4 to 15 carbon atoms, and the radicals mentioned may be fully or partially substituted by heteroatoms, —$OR^{27}$, —$SR^{27}$, —$N(R^{27})_2$, —$P(R^{27})_2$, where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$-alkyl, $C_6$–$C_{15}$-aryl, $C_3$–$C_{10}$-cycloalkyl, alkylaryl with cyclopentadienyl derivatives of alkali metals or alkaline earth metals, heating the reaction mixture obtained in this way to from −78 to 250° C., with or without addition of free radicals or free radical formers, and, if desired, subsequently replacing the bridged phenolic ligand or the two unbridged phenolic ligands to form the monosubstitution or disubstitution product; racemic metallocene complexes of the formula III

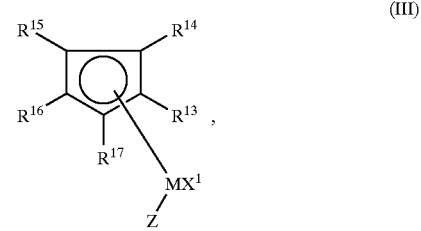

where the substituents and indices have the following meanings:

M is titanium, zirconium, hafnium, vanadium, niobium, tantalum, chromium, molybdenum, tungsten or an element of transition group III of the Periodic Table or a lanthanide, $X^1$ is

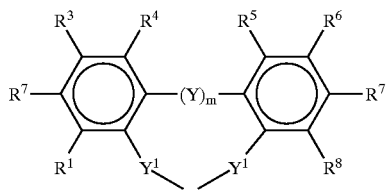

where:

$R^1$, $R^8$ are identical or different and are each hydrogen, fluorine, chlorine, bromine, iodine, $C_1$–$C_{20}$-alkyl, 3- to 8-membered cycloalkyl which may in turn bear a $C_1$–$C_{10}$-alkyl group as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $Si(R^9)_3$ where $R^9$ are identical or different and are each $C_1$–$C_{20}$-alkyl, $C_3$–$C_{10}$-cycloalkyl, $C_6$–$C_{15}$-aryl, where the radicals mentioned may be partially or fully substituted by heteroatoms, —$OR^{27}$, —$SR^{27}$, —$N(R^{27})_2$, —$P(R^{27})_2$, where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$-alkyl, $C_6$–$C_{15}$-aryl, $C_3$–$C_{10}$-cycloalkyl, alkylaryl $R^2$ to $R^7$ are identical or different and are each hydrogen, $C_1$–$C_{20}$-alkyl, 3- to 8-membered cycloalkyl which may in turn bear a $C_1$–$C_{10}$-alkyl radical as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $Si(R^9)_3$ where $R^9$ are identical or different and are each $C_1$–$C_{20}$-alkyl, $C_3$–$C_{10}$-cycloalkyl, $C_6$–$C_{15}$-aryl, where adjacent radicals $R^2$ to $R^7$ may form saturated, partially saturated or unsaturated cyclic groups having from 4 to 15 carbon atoms, and the radicals mentioned may be fully or partially substituted by heteroatoms, —$OR^{27}$, —$SR^{27}$, —$N(R^{27})_2$, —$P(R^{27})_2$, where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$-alkyl, $C_6$–$C_{15}$-aryl, $C_3$–$C_{10}$-cycloalkyl, alkylaryl Y, $Y^1$ are identical or different and are each

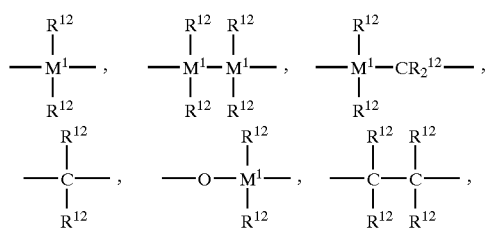

$=BR^{12}$, $=AlR^{12}$, —Ge—, —Sn—, —O—, —S—, $=SO$, $=SO_2$, $=NR^{12}$, $=CO$, $=PR^{12}$ or $=P(O)R^{12}$, where $R^{12}$ are identical or different and are each hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl, $C_7$–$C_{40}$-alkylaryl, or two radicals $R^{12}$ together with the atoms connecting them form a ring, $M^1$ is silicon, germanium or tin and m is 0, 1, 2, 3, or Y is nonbridging and represents two radicals R' and R", where R' and R" are identical or different and are each hydrogen, fluorine, chlorine, bromine, iodine, $C_1$–$C_{20}$-alkyl, 3- to 8-membered cycloalkyl which may in turn bear a $C_1$–$C_{10}$-alkyl group as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $Si(R^9)_3$ where $R^9$ are identical or different and are each $C_1$–$C_{20}$-alkyl, $C_3$–$C_{10}$-cycloalkyl, $C_6$–$C_{15}$-aryl or together with adjacent radicals $R^4$ or $R^5$ form saturated, partially saturated or unsaturated cyclic groups having from 4 to 15 carbon atoms, and the radicals mentioned may be fully or partially substituted by heteroatoms, —$OR^{27}$, —$SR^{27}$, —$N(R^{27})_2$, —$P(R^{27})_2$, where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$-alkyl, $C_6$–$C_{15}$-aryl, $C_3$–$C_{10}$-cycloalkyl, alkylaryl, $R^{13}$ to $R^{17}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{18})_3$ where $R^{18}$ are identical or different and are each $C_1$–$C_{10}$-alkyl, $C_6$–$C_{15}$-aryl or $C_3$–$C_{10}$-cycloalkyl, Z is

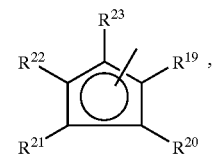

where the radicals $R^{19}$ to $R^{23}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{24})_3$ where $R^{24}$ are identical or different and are each $C_1$–$C_{10}$-alkyl, $C_6$–$C_{15}$-aryl or $C_3$–$C_{10}$-cycloalkyl, or $R^{16}$ and Z together form a -$[T(R^{25})(R^{26})]_q$-E- group in which T may be identical or different and are each silicon, germanium, tin or carbon, $R^{25}$, $R^{26}$ are each hydrogen, $C_1$–$C_{10}$-alkyl, $C_3$–$C_{10}$-cycloalkyl or $C_6$–$C_{15}$-aryl q is 1, 2, 3 or 4, E is

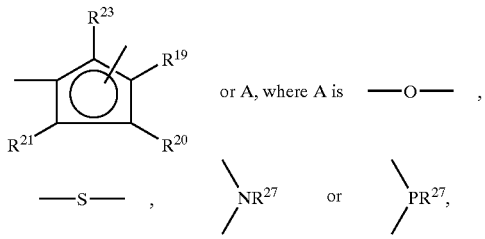

or A, where A is —O—,

—S—, \NR²⁷ or \PR²⁷,
          /       / where $R^{27}$ is $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$-alkyl, $C_6$–$C_{15}$-aryl, $C_3$–$C_{10}$-cycloalkyl or alkylaryl, and the use of racemic metallocene complexes of the formula III as catalysts or as constituents of catalysts for the polymerization of olefinically unsaturated compounds or as reagents or catalysts in stereoselective synthesis.

In addition to the stereoselective polymerization of olefins, the enantioselective synthesis of organic compounds increasingly offers interesting possible applications of chiral metallocene complexes of metals of transition groups III–VI of the Periodic Table of the Elements. Examples which may be mentioned are enantioselective hydrogenations of prochiral substrates, for example prochiral olefins, as described in R. Waymouth, P. Pino, J. Am. Chem. Soc. 112 (1990), pp. 4911–4914, or prochiral ketones, imines and oximes as described in WO 92/9545.

Further examples are the preparation of optically active alkenes by enantioselective oligomerization as described in W. Kaminsky et al., Angew. Chem. 101 (1989), pp. 1304–1306, and the enantioselective cyclopolymerization of 1,5-hexadienes as described in R. Waymouth, G. Coates, J. Am. Chem. Soc. 113 (1991), pp. 6270–6271.

The applications mentioned generally require the use of a metallocene complex in its racemic form, i.e. without meso compounds. In the case of the mixture of diastereomers (rac. and meso forms) obtained in the metallocene synthesis of the prior art, the meso form firstly has to be separated off. Since the meso form has to be discarded, the yield of racemic metallocene complex is low.

It is an object of the present invention to find a process for selectively preparing racemic metallocene complexes which are virtually free (to within NMR measurement accuracy) of meso isomer. A further object is to find racemic metallocene complexes which can either be used directly as catalysts or in catalysts, primarily for the polymerization of olefins, or can be used as catalysts or in catalysts, primarily for the polymerization of olefins, after modification, for example after replacement of an "auxilary ligand", or can be used as reagents or catalysts in stereoselective synthesis.

We have found that these objects are achieved by the process defined in the claims, by the racemic metallocene complexes III and by their use as catalysts or in catalysts for the polymerization of olefinically unsaturated compounds or as reagents or catalysts in stereoselective synthesis.

The terms "meso form", "racemate" and thus also "enantiomers" in the context of metallocene complexes are known and defined, for example, in Rheingold et al., Organometallics 11 (1992), pp. 1869–1876.

For the purposes of the present invention, the expression "virtually meso free" means that at least 90% of a compound are present in the form of the racemate.

The bridged or unbridged transition metal-aromatic complexes used according to the present ivnention have the formula I

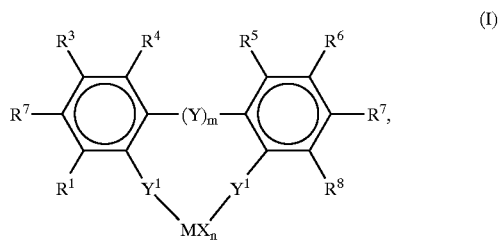

(I)

where the substituents and indices have the following meanings:

M is titanium, zirconium, hafnium, vanadium, niobium, tantalum, chromium, molybdenum, tungsten or an element of transition group III of the Periodic Table or a lanthanide, X are identical or different and are each fluorine, chlorine, bromine, iodine, hydrogen, $C_1$–$C_{10}$-alkyl, $C_6$–$C_{15}$-aryl, alkylaryl having from 1 to 10 carbon atoms in the alkyl part and from 6 to 20 carbon atoms in the aryl part, —$OR^{10}$ or —$NR^{10}R^{11}$, n is an integer from 1 to 4, where n corresponds to the valence of M minus 2, $R^1$, $R^8$ are identical or different and are each hydrogen, fluorine, chlorine, bromine, iodine, $C_1$–$C_{20}$-alkyl, 3- to 8-membered cycloalkyl which may in turn bear a $C_1$–$C_{10}$-alkyl group as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $Si(R^9)_3$ where $R^9$ are identical or different and are each $C_1$–$C_{20}$-alkyl, $C_3$–$C_{10}$-cycloalkyl, $C_6$–$C_{15}$-aryl, where the radicals mentioned may be partially or fully substituted by heteroatoms, —$OR^{27}$, —$SR^{27}$, —$N(R^{27})_2$, —$P(R^{27})_2$, where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$-alkyl, $C_6$–$C_{15}$-aryl, $C_3$–$C_{10}$-cycloalkyl, alkylaryl $R^2$ to $R^7$ are identical or different and are each hydrogen, $C_1$–$C_{20}$-alkyl, 3- to 8-membered cycloalkyl which may in turn bear a $C_1$–$C_{10}$-alkyl radical as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $Si(R_9)_3$ where $R^9$ are identical or different and are each $C_1$–$C_{20}$-alkyl, $C_3$–$C_{10}$-cycloalkyl, $C_6$–$C_{15}$-aryl, where adjacent radicals $R^2$ to $R^7$ may form saturated, partially saturated or unsaturated cyclic groups having from 4 to 15 carbon atoms, and the radicals mentioned may be fully or partially substituted by heteroatoms, —$OR^{27}$, —$SR^{27}$, —$N(R^{27})_2$, —$P(R^{27})_2$, where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$-alkyl, $C_6$–$C_{15}$-aryl, $C_3$–$C_{10}$-cycloalkyl, alkylaryl $R^{10}$, $R^{11}$ are each $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical, Y, Y$^1$ are identical or different and are each

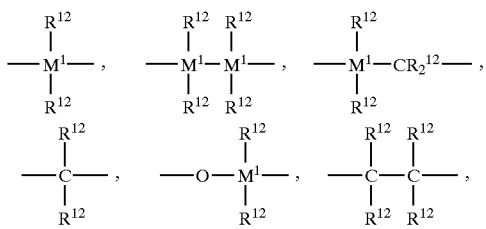

=BR$^{12}$, =AlR$^{12}$, —Ge—, —Sn—, —O—, —S—, =SO, =SO$_2$, =NR$^{12}$, =CO, =PR$^{12}$ or =P(O)R$^{12}$, where R$^{12}$ are identical or different and are each hydrogen, halogen, C$_1$–C$_{10}$-alkyl, C$_1$–C$_{10}$-fluoroalkyl, C$_6$–C$_{10}$-fluoroaryl, C$_6$–C$_{10}$-aryl, C$_1$–C$_{10}$-alkoxy, C$_2$–C$_{10}$-alkenyl, C$_7$–C$_{40}$-arylalkyl, C$_8$–C$_{40}$-arylalkenyl, C$_7$–C$_{40}$-alkylaryl, or two radicals R$^{12}$ together with the atoms connecting them form a ring, M$^1$ is silicon, germanium or tin and m is 0, 1, 2, 3, or Y is nonbridging and represents two radicals R' and R'', where R' and R'' are identical or different and are each hydrogen, fluorine, chlorine, bromine, iodine, C$_1$–C$_{20}$-alkyl, 3- to 8-membered cycloalkyl which may in turn bear a C$_1$–C$_{10}$-alkyl group as substituent, C$_6$–C$_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, Si(R$^9$)$_3$ where R$^9$ are identical or different and are each C$_1$–C$_{20}$-alkyl, C$_3$–C$_{10}$-cycloalkyl, C$_6$–C$_{15}$-aryl or together with adjacent radicals R$^4$ or R$^5$ form saturated, partially saturated or unsaturated cyclic groups having from 4 to 15 carbon atoms, and the radicals mentioned may be fully or partially substituted by heteroatoms.

—OR$^{27}$, —SR$^{27}$, —N(R$^{27}$)$_2$, —P(R$^{27}$)$_2$, where R$^{27}$ are identical or different and are each C$_1$–C$_{10}$-alkyl, C$_6$–C$_{15}$-aryl, C$_3$–C$_{10}$-cycloalkyl, alkylaryl or Si(R$^{28}$)$_3$ where R$^{28}$ are identical or different and are each C$_1$–C$_{10}$-alkyl, C$_6$–C$_{15}$-aryl, C$_3$–C$_{10}$-cycloalkyl, alkylaryl.

Preferred metals M are titanium, zirconium and hafnium, in particular zirconium.

Well-suited substituents X are fluorine, chlorine, bromine, iodine, preferably chlorine, also C$_1$–C$_6$-alkyl such as methyl, ethyl, n-propyl, isopropyl, n-butyl, sec-butyl, i-butyl, preferably tert-butyl. Further useful substituents X are alkoxides —OR$^{10}$ or amides —NR$^{10}$R$^{11}$ where R$^{10}$ or R$^{11}$ is C$_1$–C$_{10}$-alkyl, C$_6$–C$_{15}$-aryl, alkylaryl, arylalkyl, fluoroalkyl or fluoroaryl each having from 1 to 10 carbon atoms in the alkyl radical and from 6 to 20 carbon atoms in the aryl radical. Such radicals X are, for example, methyl, ethyl, i-propyl, tert-butyl, phenyl, naphthyl, p-tolyl, benzyl, trifluoromethyl, pentafluorophenyl.

The substituents R$^1$ and R$^8$ are identical or different and are each hydrogen, fluorine, chlorine, bromine, iodine, C$_1$–C$_{20}$-alkyl, —OR$^{27}$, —SR$^{27}$, —N(R$^{27}$)$_2$, —P(R$^{27}$)$_2$, where R$^{27}$ are identical or different and are each C$_1$–C$_{10}$-alkyl, C$_6$–C$_{15}$-aryl, C$_3$–C$_{10}$-cycloalkyl, alkylaryl or Si(R$^{28}$)$_3$ where R$^{28}$ are identical or different and are each C$_1$–C$_{10}$-alkyl, C$_6$–C$_{15}$-aryl, C$_3$–C$_{10}$-cycloalkyl, alkylaryl, 3- to 8-membered cycloalkyl which may in turn bear a C$_1$–C$_{10}$-alkyl radical such as methyl, ethyl or propyl as substituent.

Examples of such cycloalkyl radicals are cyclopropyl, cyclopentyl, preferably cyclohexyl, norbornyl. The substituents R$^1$ and R$^8$ may also be C$_6$–C$_{15}$-aryl such as phenyl, naphthyl; alkylaryl having from 1 to 10 carbon atoms in the alkyl part and from 6 to 20 carbon atoms in the aryl part, e.g. p-tolyl; arylalkyl having from 1 to 10 carbon atoms in the alkyl part and from 6 to 20 carbon atoms in the aryl part, e.g. benzyl, neophyl, or they may be triorganosilyl such as Si(R$^9$)$_3$ where R$^9$ are identical or different and are each C$_1$–C$_{20}$-alkyl, C$_3$–C$_{10}$-cycloalkyl, C$_6$–C$_{15}$-aryl, for example trimethylsilyl, tert-butyldimethylsilyl, triphenylsilyl. The radicals mentioned can, of course, also be partially or fully substituted by heteroatoms, for example by S-, N-, O- or halogen-containing structural elements. Examples of such substituted radicals R$^1$ and R$^8$ are the trifluoromethyl, pentafluoroethyl, heptafluoropropyl, heptafluoroisopropyl and pentafluorophenyl groups.

Preferred substituents R$^1$ and R$^8$ are those which take up a large amount of space. Such substituents are usually referred to as bulky substituents and they can cause steric hindrance.

For the purposes of the present invention, these groups are generally organic or organosilicon radicals which take up a large amount of space (bulky radicals), but also fluorine and preferably chlorine, bromine and iodine. The number of carbon atoms in such organic or organosilicon radicals is usually not less than three.

Preferred nonaromatic, bulky radicals are organic or organosilicon radicals which are branched in the α position or a higher position. Examples of such radicals are branched C$_3$–C$_{20}$-aliphatic, C$_9$–C$_{20}$-araliphatic and C$_3$–C$_{10}$-cycloaliphatic radicals, e.g. isopropyl, tert-butyl, isobutyl, neopentyl, 2-methyl-2-phenylpropyl (neophyl), cyclohexyl, 1-methylcyclohexyl, bicyclo[2.2.1]hept-2-yl (2-norbornyl), bicyclo[2.2.1]hept-1-yl (1-norbornyl), adamantyl. Further suitable radicals of this type are organosilicon radicals having from three to thirty carbon atoms, for example trimethylsilyl, triethylsilyl, triphenylsilyl, tert-butyldimethylsilyl, tritolylsilyl or bis(trimethylsilyl)methyl.

Preferred aromatic, bulky groups are generally C$_6$–C$_{20}$-aryl radicals, such as phenyl, 1- or 2-naphthyl or preferably C$_1$–C$_{10}$-alkyl- or C$_3$–C$_{10}$-cycloalkyl-substituted aromatic radicals such as 2,6-dimethylphenyl, 2,6-di-tert-butylphenyl, mesityl.

Very particularly preferred substituents R$^1$ and R$^8$ are i-propyl, tert-butyl, trimethylsilyl, cyclohexyl, i-butyl, trifluoromethyl, 3,5-dimethylphenyl.

In the preferred substitution pattern, R$^1$ and R$^8$ in formula I are identical.

The substituents R$^2$ to R$^7$ are identical or different and are each hydrogen, C$_1$–C$_{20}$-alkyl, —OR$^{27}$, —SR$^{27}$, —N(R$^{27}$)$_2$, —P(R$^{27}$)$_2$, where R$^{27}$ are identical or different and are each C$_1$–C$_{10}$-alkyl, C$_6$–C$_{15}$-aryl, C$_3$–C$_{10}$-cycloalkyl, alkylaryl or Si(R$^{28}$)$_3$ where R$^{28}$ are identical or different and are each C$_1$–C$_{10}$-alkyl, C$_6$–C$_{15}$-aryl, C$_3$–C$_{10}$-cycloalkyl, alkylaryl, 3- to 8-membered cycloalkyl which may in turn bear a C$_1$–C$_{10}$-alkyl radical such as methyl, ethyl or propyl as substituent. Examples of such cycloalkyl radicals are cyclopropyl, cyclopentyl, preferably cyclohexyl, norbornyl. The substituents R$^2$ to R$^7$ may also be C$_6$–C$_{15}$-aryl such as phenyl, naphthyl, alkylaryl having from 1 to 10 carbon atoms in the alkyl part and from 6 to 20 carbon atoms in the aryl part, e.g. p-tolyl, arylalkyl having from 1 to 10 carbon atoms in the alkyl part and from 6 to 20 carbon atoms in the aryl part, e.g. benzyl, neophyl, or they may be triorganosilyl such as Si(R$^9$)$_3$ where R$^9$ are identical or different and are each C$_1$–C$_{20}$-alkyl, C$_3$–C$_{10}$-cycloalkyl, C$_6$–C$_{15}$-aryl, for example trimethylsilyl, tert-butyldimethylsilyl, triphenylsilyl. The radicals R$^2$ to R$^7$ may also be connected to one another so that adjacent radicals form saturated, partially saturated or unsaturated cyclic groups having from 4 to 15 carbon atoms. Preferably, the radicals $R^3$ and $R^4$ and/or the radicals $R^5$ and $R^6$ are joined by a $C_2$ bridge so as to form a benzo-fused ring system (naphthyl derivative). The abovementioned radicals $R^2$ to $R^7$ can, of course, also be partially or fully substituted by heteroatoms, for example by S-, N-, O- or halogen-containing structural elements. Examples of such substituted radicals $R^2$ to $R^7$ are the trifluoromethyl, pentafluoroethyl, heptafluoropropyl, heptafluoroisopropyl and pentafluorophenyl groups.

Particular preference is given to the radicals $R^2$ and $R^7$ being identical and each being hydrogen and $R^3$, $R^4$, $R^5$, $R^6$ each being as defined above.

Possible bridging elements Y, $Y^1$ are the following:

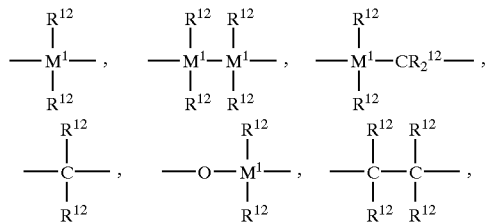

$=BR^{12}$, $=AlR^{12}$, $-Ge-$, $-Sn-$, $-O-$, $-S-$, $=SO$, $=SO_2$, $=NR^{12}$, $=CO$, $=PR^{12}$ or $=P(O)R^{12}$, where $R^{12}$ are identical or different and are each a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group or $R^{12}$ and $R^{13}$ or $R^{12}$ and $R^{14}$, in each case together with the atoms connecting them, form a ring, $M^1$ is silicon, germanium or tin.

A ring structure in (I) (m ≠0) is of advantage for the process of the invention, and ring sizes where m=1 to 3 are preferred.

Preferred bridging elements Y, $Y^1$ are methylene $-CH_2-$, S, O, $-C(CH_3)_2-$, where m in formula I is preferably 1 or 2; $Y^1$ are very particularly preferably identical and are each oxygen $-O-$. Preference is also given to phenoxide-type structures in which m in formula I is 0, i.e. the aromatic ring systems are linked directly to one another, preferably to form a biphenol derivative.

Among the unbridged transition metal-aromatic complexes of the formula I which can be used according to the present invention, preference is given to those in which Y represents radicals R' and R" which are identical or different and are each fluorine, chlorine, bromine, iodine, $-OR^{27}$, $-SR^{27}$, $-N(R^{27})_2$, $-P(R^{27})_2$, where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$-alkyl, $C_6$–$C_{15}$-aryl, $C_3$–$C_{10}$-cycloalkyl, alkylaryl, $C_1$–$C_{20}$-alkyl or 3- to 8-membered cycloalkyl which may in turn bear a $C_1$–$C_{10}$-alkyl radical such as methyl, ethyl or propyl as substituent. Examples of such cycloalkyl radicals are cyclopropyl, cyclopentyl, preferably cyclohexyl, norbornyl. The substituents R' and R" may also be $C_6$–$C_{15}$-aryl such as phenyl, naphthyl; alkylaryl having from 1 to 10 carbon atoms in the alkyl part and from 6 to 20 carbon atoms in the aryl part, e.g. p-tolyl; arylalkyl having from 1 to 10 carbon atoms in the alkyl part and from 6 to 20 carbon atoms in the aryl part, e.g. benzyl, neophyl, or they may be triorganosilyl such as $Si(R^9)_3$ where $R^9$ are identical or different and are each $C_1$–$C_{20}$-alkyl, $C_3$–$C_{10}$-cycloalkyl, $C_6$–$C_{15}$-aryl, for example trimethylsilyl, tert-butyldimethylsilyl, triphenylsilyl. The radicals mentioned can, of course, also be partially or fully substituted by heteroatoms, for example by S-, N-, O- or halogen-containing structural elements. Examples of such substituted radicals R' and R" are the trifluoromethyl, pentafluoroethyl, heptafluoropropyl, heptafluoroisopropyl and pentafluorophenyl groups.

R' and R" are preferably identical. Particularly preferred unbridged transition metal-aromatic complexes are ones in which $R^1$, $R^8$, R' and R" are identical; a very particularly preferred substitution pattern is one in which $R^1$, $R^3$, R' and $R^6$, $R^8$, R" are H and $R^2$, $R^4$ and $R^5$, $R^7$ are as defined above, preferably tert-butyl, but are not H. The phenolic group in (I) is preferably a biphenoxide group having the above-described substitution pattern.

The bridged or unbridged transition metal-aromatic complexes I are generally prepared by methods known to those skilled in the art.

The synthesis of bridged transition metal phenoxide complexes is described, for example, in C. J. Schaverien, J. Am. Chem. Soc. (1995), pages 3008 to 3012. Another procedure which has been found to be useful is the following, where the reaction is generally carried out at from −78 to 110° C., preferably initially at about 20° C. and then under reflux to complete the reaction. The biphenol is firstly deprotonated in a solvent, for example tetrahydrofuran (THF), for example using sodium hydride or n-butyllithium, and the transition metal compound, for example the halide, e.g. titanium, zirconium or hafnium tetrachloride, advantageously in the form of the bis-THF adduct, is then added. After the reaction is complete, the product is generally obtained by separating off salts and then crystallizing it. The preparation of unbridged transition metal phenoxide complexes can be carried out, for example, as described by H. Yasuda et al., J. Organomet. Chem. 473 (1994), pages 105 to 116.

The bridged or unbridged transition metal-aromatic complexes I generally additionally contain from 1 to 4 equivalents of a Lewis base which is generally introduced via the synthetic route. Examples of such Lewis bases are ethers such as diethyl ether or tetrahydrofuran (THF) or amines such as TMEDA. However, it is also possible to obtain the transition metal-aromatic complexes in a form free of Lewis bases, for example by drying under reduced pressure or by choice of other solvents in the synthesis. Such measures are known to those skilled in the art.

The racemic metallocene complexes of the present invention are prepared by reacting the bridged or unbridged transition metal-aromatic complexes I with cyclopentadienyl derivatives of alkali metals or alkaline earth metals and subsequently heating the resulting reaction mixture in the presence or absence of free radicals or free radical formers, as described below.

Preference is given to using transition metal-aromatic complexes I in which M is zirconium and the radicals $R^1$ and $R^8$ have the preferred meanings described above. Very well-suited complexes are dichlorobis(3,5-di-tert-butylphenolato)zirconium.(THF)$_2$, dichlorobis(3,5-di-tert-butylphenolato)zirconium.(DME), dichlorobis(2,6-dimethylphenolato)zirconium.(THF)$_2$, dichlorobis(2,6-dimethylphenolato) zirconium.(DME), dichlorobis(2,4,6-trimethylphenolato) zirconium.(THF)$_2$, dichlorobis(2,4,6-trimethylphenolato) zirconium.(DME) and the zirconium phenoxide compounds mentioned in the example.

Suitable cyclopentadienyl derivatives of alkali metals or alkaline earth metals are in principle those which, after reaction with the bridged transition metal-aromatic complexes I used according to the present invention, selectively give racemic metallocene complexes which are virtually free of meso isomer.

The racemic metallocene complexes of the present invention can be bridged, but do not have to be. In general, a high barrier to rotation, especially in the temperature range from 20 to 80° C., (able to be determined by $^1$H- and/or $^{13}$C-NMR spectroscopy) of the unbridged cyclopentadienyl-type ligands in the metallocene is sufficient for the metallocene complexes to be able to be isolated in their racemic form without them being able to transform into the meso form. The barrier to rotation which ensures this is usually above 20 kJ/mol.

Well-suited cyclopentadienyl derivatives of alkali metals or alkaline earth metals are those of the formula II

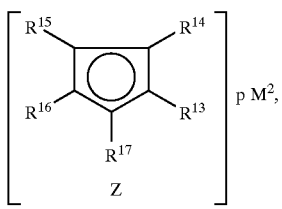

where the substituents and indices have the following meanings:

$M^2$ is Li, Na, K, Rb, Cs, Be, Mg, Ca, Sr, Ba, $R^{13}$ to $R^{17}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{18})_3$ where $R^{18}$ are identical or different and are each $C_1$–$C_{10}$-alkyl, $C_6$–$C_{15}$-aryl or $C_3$–$C_{10}$-cycloalkyl, Z is

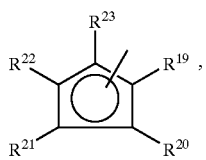

where the radicals $R^{19}$ to $R^{23}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{24})_3$ where $R^{24}$ are identical or different and are each $C_1$–$C_{10}$-alkyl, $C_6$–$C_{15}$-aryl or $C_3$–$C_{10}$-cycloalkyl, or $R^{16}$ and Z together form a -[T($R^{25}$)($R^{26}$)]$_n$-E- group in which T may be identical or different and are each silicon, germanium, tin or carbon, $R^{25}$, $R^{26}$ are each hydrogen, $C_1$–$C_{10}$-alkyl, $C_3$–$C_{10}$-cycloalkyl or $C_6$–$C_{15}$-aryl n is 1, 2, 3 or 4, E is

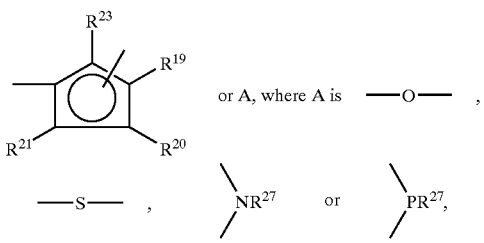

where $R^{27}$ is $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$-alkyl, $C_6$–$C_{15}$-aryl, $C_3$–$C_{10}$-cycloalkyl or alkylaryl, where p=1 for Be, Mg, Ca, Sr, Ba and p=2 for Li, Na, K, Rb, Cs.

Preferred compounds of the formula II are those in which $M^2$ is lithium, sodium or, in particular magnesium. Particular preference is also given to compounds of the formula II a)

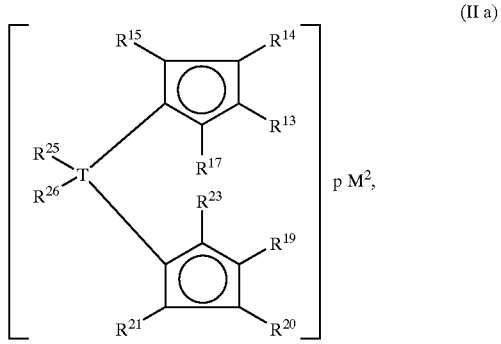

in which $M^2$ is magnesium, $R^{17}$ and $R^{23}$ are substituents other than hydrogen, e.g. $C_1$–$C_{10}$-alkyl, such as methyl, ethyl, n-propyl, i-propyl, n-butyl, sec-butyl, tert-butyl, i-butyl, hexyl, also $C_6$–$C_{10}$-aryl such as phenyl or trialkylsilyl such as trimethylsilyl, T($R^{25}R^{26}$) is bis-$C_1$–$C_{10}$-alkylsilyl or bis-$C_6$–$C_{10}$-arylsilyl such as dimethylsilyl, diphenylsilyl, also 1,2-ethanediyl, methylene, and the radicals $R^{13}$ to $R^{15}$ and $R^{19}$ to $R^{25}$ are as defined above and in particular form an indenyl-type ring system or a benzoindenyl-type ring system.

Very particularly preferred compounds II are those which are described in the examples and also dimethylsilanediylbis(3-tert-butyl-5-methylcyclopentadienyl)magnesium diethylsilanediylbis(3-tert-butyl-5-methylcyclopentadienyl) magnesium dimethylsilanediylbis(3-tert-butyl-5-ethylcyclopentadienyl) magnesium dimethylsilanediylbis(3-tert-pentyl-5-methylcyclopentadienyl)magnesium dimethylsilanediylbis(2,4,7-trimethylindenyl)magnesium 1,2-ethanediylbis(1-{2,4,7-trimethylindenyl})magnesium dimethylsilanediylbis(1-indenyl)magnesium dimethylsilanediylbis(4,5,6,7-tetrahydro-1-indenyl)magnesium dimethylsilanediylbis(2-methylindenyl)magnesium phenyl(methyl)silanediylbis(2-methylindenyl)magnesium diphenylsilanediylbis(2-methylindenyl)magnesium dimethylsilanediylbis(2-methyl-4,5,6,7-tetrahydro-1-indenyl)magnesium
dimethylsilanediylbis(2,4-dimethyl-6-isopropylindenyl)magnesium
dimethylsilanediylbis(2-methyl-1-benzindenyl)magnesium
dimethylsilanediylbis(2-ethyl-1-benzindenyl)magnesium
dimethylsilanediylbis(2-propyl-1-benzindenyl)magnesium
dimethylsilanediylbis(2-phenyl-1-benzindenyl)magnesium
diphenylsilanediylbis(2-methyl-1-benzindenyl)magnesium
phenylmethylsilanediylbis(2-methyl-1-benzindenyl)magnesium
ethanediylbis(2-methyl-1-benzindenyl)magnesium
dimethylsilanediylbis(2-methyl-1-tetrahydrobenzindenyl)magnesium
dimethylsilanediylbis(2-methyl-4-isopropyl-1-indenyl)magnesium
dimethylsilanediylbis(2-methyl-4-phenyl-1-indenyl)magnesium
dimethylsilanediylbis(2-methyl-4-naphthyl-1-indenyl)magnesium
dimethylsilanediylbis(2-methyl-4-{3,5-trifluoromethyl}phenyl-1-indenyl)magnesium
dimethylsilanediylbis(2-ethyl-4-isopropyl-1-indenyl)magnesium
dimethylsilanediylbis(2-ethyl-4-phenyl-1-indenyl)magnesium
dimethylsilanediylbis(2-ethyl-4-naphthyl-1-indenyl)magnesium
dimethylsilanediylbis(2-ethyl-4-{3,5-trifluoromethyl}phenyl-1-indenyl)magnesium
ethanediylbis(2-methyl-4-phenyl-1-indenyl)magnesium
ethanediylbis(2-methyl-4-naphthyl-1-indenyl)magnesium
ethanediylbis(2-methyl-4-{3,5-di-(trifluoromethyl)}phenyl-1-indenyl)magnesium
dimethylsilanediylbis(2-methyl-4-(4'-tert-butylphenyl)indenyl)magnesium
dimethylsilanediylbis(2-methyl-4-(4'-tert-butylphenyl)-indenyl)-(2-isopropyl-4-(4'-tert-butylphenyl)indenyl)magnesium
dimethylsilanediylbis(2-cyclohexyl-4-phenylindenyl)magnesium
dimethylsilanediylbis(2-butyl-4-phenylindenyl)magnesium
dimethylsilanediylbis(2-ethyl-4-(4'-tert-butylphenyl)indenyl)magnesium
dimethylsilanediylbis(2-propyl-4-(4'-tert-butylphenyl)indenyl)magnesium
dimethylgermanediylbis(2-meth-4-(4'-tert-butylphenyl)indenyl)magnesium
diethylsilanediylbis(2-methyl-4-(4'-tert-butylphenyl)indenyl)magnesium
dimethylsilanediylbis(2-butyl-4-(4'-tert-butylphenyl)indenyl)magnesium
dimethylsilanediyl(2-methyl-4-(4'-tert-butylphenyl)indenyl)-(4-(4'-tert-butylphenyl)indenyl)magnesium
dimethylsilanediylbis(2-butyl-4-(4'-tert-butylphenyl-6-(4'-tert-butylphenyl)indenyl)magnesium
dimethylsilanediylbis(2-isopropyl-4-(4'-tert-butylphenyl)indenyl)magnesium
dimethylsilanediylbis(2-isopropyl-4-(4'-tert-butylphenyl)indenyl)magnesium
dimethylsilanediyl(2-ethyl-4-(4'-tert-butylphenyl)indenyl)-2-isopropyl-4-(4'-tert.-butylphenyl)indenyl)magnesium
dimethylsilanediyl(2-methyl-4-naphthylindenyl)-(2-isopropyl-4-(4'-tert-butylphenyl)indenyl)magnesium
and the respective Lewis base adducts of these compounds with, for example, THF, DME, TMEDA.

Such alkali or alkaline earth metal compounds II can be obtained by methods known from the literature, for example by the, preferably, stoichiometric, reaction of an organometallic compound or a hydride of the alkali metal or alkaline earth metal with the appropriate cyclopentadiene-type hydrocarbon. Suitable organometallic compounds are, for example, n-butyllithium, di-n-butylmagnesium or (n,s)-dibutylmagnesium (Bomag).

The reaction of the bridged or unbridged transition metal-aromatic complexes I with the cyclopentadienyl derivatives of alkali or alkaline earth metals, preferably of the formulae II or II a) usually takes place in an organic solvent or suspension medium, preferably in a solvent mixture comprising a Lewis-basic solvent, at from −78° C. to 250° C., preferably from 0 to 110° C. Well-suited solvents are aliphatic hydrocarbons such as pentane, hexane, heptane, aromatic hydrocarbons such as toluene, ortho-, meta- or para-xylene or isopropylbenzene (cumene), ethers such as tetrahydrofuran (THF), diethyl ether, methyl tert-butyl ether or dimethoxyethane (DME), amines such as diisopropylamine, tetramethylethanediamine (TMEDA) or pyridine. Well-suited solvent mixtures are mixtures of toluene and THF, toluene and DME or toluene and TMEDA, where the Lewis base is generally present in an amount of from 0.1 to 50 mol %, preferably from 1 to 20 mol %, based on the solvent mixture. The molar ratio of the transition metal-aromatic complex I to the cyclopentadienyl derivative of an alkali or alkaline earth metal is usually in the range from 0.8:1 to 1:1.2 and is preferably 1:1.

It has been found that subsequent warming or heating of the reaction mixture to temperatures in the range from −78 to 250° C., preferably from 20 to 150° C. and in particular from 80 to 110° C., in the presence or absence of free radicals or free radical formers quickly leads to a higher yield, generally from 80 to 100%, preferably from 95 to 100%, of racemic complexes (I). Possible free radicals are oxygen and 2,2'-6,6'-tetramethylpyrimidine N-oxide (TEMPO). As free radical formers, it is possible to use all organic and inorganic compounds which decompose to generate free radicals in the abovementioned temperature range and/or on irradiation, for example peroxides, diacyl peroxides (e.g. benzoyl peroxide, acetyl peroxide), peroxydicarbonates, peresters, azoalkanes, nitrites, hypochlorites, polyhalomethanes, N-chloroamines. Particular preference is given to using TEMPO. Preference is given to using free radical formers when the metallocene (I) contains a benzo-fused indenyl system such as dimethylsilylbis(2-methylbenzoindenyl) as cyclopentadienyl-type ligand.

The racemic metallocene complexes prepared according to the present invention are preferably complexes of the formula III

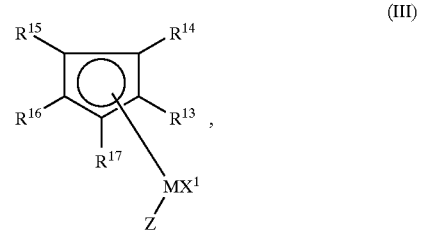

where the substituents and indices have the following meanings:
M is titanium, zirconium, hafnium, vanadium, niobium, tantalum, chromium, molybdenum, tungsten or an element of transition group III of the Periodic Table or a lanthanide, $X^1$

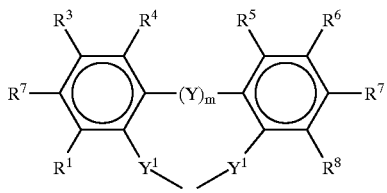

where:

$R^1$, $R^8$ are identical or different and are each hydrogen, fluorine, chlorine, bromine, iodine, $C_1$–$C_{20}$-alkyl, 3- to 8-membered cycloalkyl which may in turn bear a $C_1$–$C_{10}$-alkyl group as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $Si(R^9)_3$ where $R^9$ are identical or different and are each $C_1$–$C_{20}$-alkyl, $C_3$–$C_{10}$-cycloalkyl, $C_6$–$C_{15}$-aryl, where the radicals mentioned may be partially or fully substituted by heteroatoms, —$OR^{27}$, —$SR^{27}$, —$N(R^{27})_2$, —$P(R^{27})_2$, where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$-alkyl, $C_6$–$C_{15}$-aryl, $C_3$–$C_{10}$-cycloalkyl, alkylaryl $R^2$ to $R^7$ are identical or different and are each hydrogen, $C_1$–$C_{20}$-alkyl, 3- to 8-membered cycloalkyl which may in turn bear a $C_1$–$C_{10}$-alkyl radical as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $Si(R^9)_3$ where $R^9$ are identical or different and are each $C_1$–$C_{20}$-alkyl, $C_3$–$C_{10}$-cycloalkyl, $C_6$–$C_{15}$-aryl, where adjacent radicals $R^2$ to $R^7$ may form saturated, partially saturated or unsaturated cyclic groups having from 4 to 15 carbon atoms, and the radicals mentioned may be fully or partially substituted by heteroatoms, —$OR^{27}$, —$SR^{27}$, —$N(R^{27})_2$, —$P(R^{27})_2$, where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$-alkyl, $C_6$–$C_{15}$-aryl, $C_3$–$C_{10}$-cycloalkyl, alkylaryl $Y$, $Y^1$ are identical or different and are each

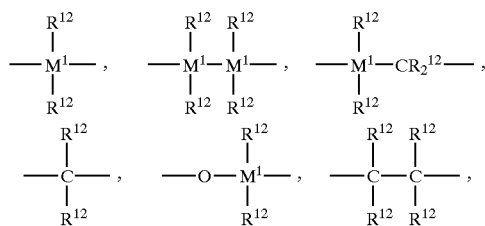

=$BR^{12}$, =$AlR^{12}$, —Ge—, —Sn—, —O—, —S—, =SO, =SO$_2$, =$NR^{12}$, =CO, =$PR^{12}$ or =$P(O)R^{12}$, where $R^{12}$ are identical or different and are each hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl, $C_7$–$C_{40}$-alkylaryl, or two radicals $R^{12}$ together with the atoms connecting them form a ring, $M^1$ is silicon, germanium or tin and m is 0, 1, 2, 3, or Y is nonbridging and represents two radicals R' and R", where R' and R" are identical or different and are each hydrogen, fluorine, chlorine, bromine, iodine, $C_1$–$C_{20}$-alkyl, 3- to 8-membered cycloalkyl which may in turn bear a $C_1$–$C_{10}$-alkyl group as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $Si(R^9)_3$ where $R^9$ are identical or different and are each $C_1$–$C_{20}$-alkyl, $C_3$–$C_{10}$-cycloalkyl, $C_6$–$C_{15}$-aryl or together with adjacent radicals $R^4$ or $R^5$ form saturated, partially saturated or unsaturated cyclic groups having from 4 to 15 carbon atoms, and the radicals mentioned may be fully or partially substituted by heteroatoms, —$OR^{27}$, —$SR^{27}$, —$N(R^{27})_2$, —$P(R^{27})_2$, where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$-alkyl, $C_6$–$C_{15}$-aryl, $C_3$–$C_{10}$-cycloalkyl, alkylaryl $R^{13}$ to $R^{17}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{18})_3$ where $R^{18}$ are identical or different and are each $C_1$–$C_{10}$-alkyl, $C_6$–$C_{15}$-aryl or $C_3$–$C_{10}$-cycloalkyl, Z is

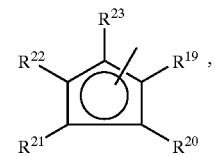

where the radicals $R^{19}$ to $R^{23}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms or $Si(R^{24})_3$ where $R^{24}$ are identical or different and are each $C_1$–$C_{10}$-alkyl, $C_6$–$C_{15}$-aryl or $C_3$–$C_{10}$-cycloalkyl, or $R^{16}$ and Z together form a -[$T(R^{25})(R^{26})$]$_q$-E- group in which T may be identical or different and are each silicon, germanium, tin or carbon, $R^{25}$, $R^{26}$ are each hydrogen, $C_1$–$C_{10}$-alkyl, $C_3$–$C_{10}$-cycloalkyl or $C_6$–$C_{15}$-aryl q is 1, 2, 3 or 4, E is

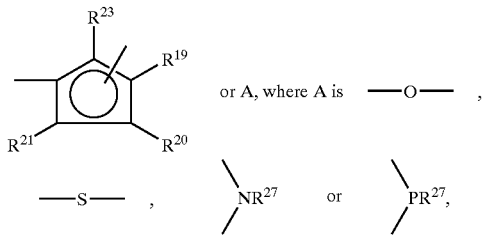

or A, where A is —O—,

—S—, $\diagdown NR^{27}$ or $\diagdown PR^{27}$, where $R^{27}$ is $C_1$–$C_{10}$-alkyl, $C_6$–$C_{15}$-aryl, $C_3$–$C_{10}$-cycloalkyl, alkylaryl or $Si(R^{28})_3$
where $R^{28}$ are identical or different and are each $C_1$–$C_{10}$-alkyl, $C_6$–$C_{15}$-aryl, $C_3$–$C_{10}$-cycloalkyl or alkylaryl.

Preferred compounds of the formula III are those in which M is titanium, hafnium or, in particular, zirconium. Furthermore, particular preference is given to bridged compounds of the formula III (ansa metallocenes) in which $R^{17}$ and $R^{23}$ are substituents other than hydrogen, for example $C_1$–$C_{10}$-alkyl such as methyl, ethyl, n-propyl, i-propyl, n-butyl, sec-butyl, tert-butyl, i-butyl, hexyl, also $C_6$–$C_{10}$-aryl such as phenyl or trialkylsilyl such as trimethylsilyl, $T(R^{25}R^{26})$ is bis-$C_1$–$C_{10}$-alkylsilyl or bis-$C_6$–$C_{10}$-arylsilyl such as dimethylsilyl, diphenylsilyl, also 1,2-ethanediyl, methylene, and the radicals $R^{13}$ to $R^{15}$ and $R^{19}$ to $R^{25}$ are as defined above and in particular form an indenyl-type ring system or a benzoindenyl-type ring system.

Very particularly preferred compounds III are those which are described in the examples, and also
dimethylsilanediylbis(3-tert-butyl-5-methylcyclopentadienyl)zirconium 3,3',5,5'-tetra-t-butyl-1,1'-bi-2-phenoxide
diethylsilanediylbis(3-tert-butyl-5-methylcyclopentadienyl) zirconium 3,3',5,5'-tetra-t-butyl-1,1'-bi-2-phenoxide
dimethylsilanediylbis(3-tert-butyl-5-ethylcyclopentadienyl) zirconium 3,3',5,5'-tetra-t-butyl-1,1'-bi-2-phenoxide
dimethylsilanediylbis(3-tert-pentyl-5-methylcyclopentadienyl)zirconium 3,3',5,5'-tetra-t-butyl-1,1'-bi-2-phenoxide
dimethylsilanediylbis(2,4,7-trimethylindenyl)zirconium 3,3',5,5'-tetra-t-butyl-1,1'-bi-2-phenoxide
1,2-ethanediylbis(1-{2,4,7-trimethylindenyl})zirconium 3,3',5,5'-tetra-t-butyl-1,1'-bi-2-phenoxide
dimethylsilanediylbis(1-indenyl)zirconium 3,3',5,5'-tetra-t-butyl-1,1'-bi-2-phenoxide
dimethylsilanediylbis(4,5,6,7-tetrahydro-1-indenyl)zirconium 3,3',5,5'-tetra-t-butyl-1,1'-bi-2-phenoxide
dimethylsilanediylbis(2-methylindenyl)zirconium 3,3',5,5'-tetra-t-butyl-1,1'-bi-2-phenoxide
phenyl(methyl)silanediylbis(2-methylindenyl)zirconium 3,3',5,5'-tetra-t-butyl-1,1'-bi-2-phenoxide
diphenylsilanediylbis(2-methylindenyl)zirconium 3,3',5,5'-tetra-t-butyl-1,1'-bi-2-phenoxide
dimethylsilanediylbis(2-methyl-4,5,6,7-tetrahydro-1-indenyl)zirconium 3,3',5,5'-tetra-t-butyl-1,1'-bi-2-phenoxide
dimethylsilanediylbis(2,4-dimethyl-6-isopropylindenyl)zirconium 3,3',5,5'-tetra-t-butyl-1,1'-bi-2-phenoxide
dimethylsilanediylbis(2-methyl-1-benzindenyl)zirconium 3,3',5,5'-tetra-t-butyl-1,1'-bi-2-phenoxide
dimethylsilanediylbis(2-ethyl-1-benzindenyl)zirconium 3,3',5,5'-tetra-t-butyl-1,1'-bi-2-phenoxide
dimethylsilanediylbis(2-propyl-1-benzindenyl)zirconium 3,3',5,5'-tetra-t-butyl-1,1'-bi-2-phenoxide
dimethylsilanediylbis(2-phenyl-1-benzindenyl)zirconium 3,3',5,5'-tetra-t-butyl-1,1'-bi-2-phenoxide
diphenylsilanediylbis(2-methyl-1-benzindenyl)zirconium 3,3',5,5'-tetra-t-butyl-1,1'-bi-2-phenoxide
phenylmethylsilanediylbis(2-methyl-1-benzindenyl)zirconium 3,3',5,5'-tetra-t-butyl-1,1'-bi-2-phenoxide
ethanediylbis(2-methyl-1-benzindenyl)zirconium 3,3',5,5'-tetra-t-butyl-1,1'-bi-2-phenoxide
dimethylsilanediylbis(2-methyl-1-tetrahydrobenzindenyl) zirconium 3,3',5,5'-tetra-t-butyl-1,1'-bi-2-phenoxide
dimethylsilanediylbis(2-methyl-4-isopropyl-1-indenyl)zirconium 3,3',5,5'-tetra-t-butyl-1,1'-bi-2-phenoxide
dimethylsilanediylbis(2-methyl-4-phenyl-1-indenyl)zirconium 3,3',5,5'-tetra-t-butyl-1,1'-bi-2-phenoxide
dimethylsilanediylbis(2-methyl-4-naphthyl-1-indenyl)zirconium 3,3',5,5'-tetra-t-butyl-1,1'-bi-2-phenoxide
dimethylsilanediylbis(2-methyl-4-{3,5-trifluoromethyl}-phenyl-1-indenyl)zirconium 3,3',5,5'-tetra-t-butyl-1,1'-bi-2-phenoxide
dimethylsilanediylbis(2-ethyl-4-isopropyl-1-indenyl)zirconium 3,3',5,5'-tetra-t-butyl-1,1'-bi-2-phenoxide
dimethylsilanediylbis(2-ethyl-4-phenyl-1-indenyl)zirconium 3,3',5,5'-tetra-t-butyl-1,1'-bi-2-phenoxide
dimethylsilanediylbis(2-ethyl-4-naphthyl-1-indenyl)zirconium 3,3',5,5'-tetra-t-butyl-1,1'-bi-2-phenoxide
dimethylsilanediylbis(2-ethyl-4-{3,5-trifluoromethyl}-phenyl-1-indenyl)zirconium 3,3',5,5'-tetra-t-butyl-1,1'-bi-2-phenoxide
ethanediylbis(2-methyl-4-phenyl-1-indenyl)zirconium 3,3',5,5'-tetra-t-butyl-1,1'-bi-2-phenoxide
ethanediylbis(2-methyl-4-naphthyl-1-indenyl)zirconium 3,3',5,5'-tetra-t-butyl-1,1'-bi-2-phenoxide
ethanediylbis(2-methyl-4-{3,5-di-(trifluoromethyl)}phenyl-1-indenyl)zirconium 3,3',5,5'-tetra-t-butyl-1,1'-bi-2-phenoxide
dimethylsilanediylbis(2-methyl-4-(4'-tert-butylphenyl)indenyl)zirconium 3,3',5,5'-tetra-tBu-1,1'-bi-2-phenoxide
dimethylsilanediyl(2-methyl-4-(4'-tert-butylphenyl)indenyl)-(2-isopropyl-4-(4'-tert-butylphenyl)indenyl)zirconium 3,3',5,5'-tetra-tBu-1,1'-bi-2-phenoxide
dimethylsilanediylbis(2-cyclohexyl-4-phenylindenyl)zirconium 3,3'5,5'-tetra-tBu-1,1'-bi-2-phenoxide
dimethylsilanediylbis(2-butyl-4-phenyl-indenyl)zirconium 3,3'5,5'-tetra-tBu-1,1'-bi-2-phenoxide
dimethylsilanediylbis(2-ethyl-4-(4'-tert-butylphenyl)indenyl)zirconium 3,3'5,5'-tetra-tBu-1,1'-bi-2-phenoxide
dimethylsilanediylbis(2-propyl-4-(4'-tert-butylphenyl)indenyl)zirconium 3,3'5,5'-tetra-tBu-1,1'-bi-2-phenoxide
dimethylgermanediylbis(2-methyl-4-(4'-tert-butylphenyl)indenyl)zirconium 3,3'5,5'-tetra-tBu-1,1'-bi-2-phenoxide
diethylsilanediylbis(2-methyl-4-(4'-tert-butylphenyl)indenyl)zirconium 3,3'5,5'-tetra-tBu-1,1'-bi-2-phenoxide
dimethylsilanediylbis(2-butyl-4-(4'-tert-butylphenyl)indenyl)zirconium 3,3'5,5'-tetra-tBu-1,1'-bi-2-phenoxide
dimethylsilanediyl(2-methyl-4-(4'-tert-butylphenyl)indenyl)-4-(4'-tert-butylphenyl)indenyl)zirconium 3,3'5,5'-tetra-tBu-1,1'-bi-2-phenoxide
dimethylsilanediylbis(2-butyl-4-(4'-tert-butylphenyl)-6-(4'-tert-butylphenyl)indenyl)zirconium 3,3'5,5'-tetra-tBu-1,1'-bi-2-phenoxide
dimethylsilanediylbis(2-isopropyl-4-(4'-tert-butylphenyl)indenyl)zirconium 3,3'5,5'-tetra-tBu-1,1'-bi-2-phenoxide
dimethylsilanediyl(2-ethyl-4-(4'-tert-butylphenyl)indenyl)(2-isopropyl-4-(4'-tert-butylphenyl)indenyl)zirconium 3,3'5,5'-tetra-tBu-1,1'-bi-2-phenoxide
dimethylsilanediyl(2-methyl-4-naphthylindenyl)-(2-isopropyl-4-(4'-tert-butylphenyl)indenyl)zirconium 3,3'5,5'-tetra-tBu-1,1'-bi-2-phenoxide The racemic metallocene complexes, preferably those of the formula III, can generally be modified further.

In particular, a bridged biphenoxide ligand $X^1$ in the complex III can be completely or half split or one or both unbridged phenoxide ligands can be split off by monosubstitution or disubstitution and, if desired, used further. Suitable splitting-off (replacement) methods are reaction of the racemic metallocene compounds, preferably those of the formula III, with $SOCl_2$, silicon tetrachloride, methylaluminum dichloride, dimethylaluminum chloride, aluminum trichloride or a Brönsted acid such as a hydrogen halide, i.e. HF, HBr, HI, preferably HCl, which is generally used as such or as a solution in water or organic solvents such as diethyl ether or THF. Well-suited solvents are aliphatic hydrocarbons such as pentane, hexane, heptane, aromatic hydrocarbons such as toluene, ortho-, meta- or para-xylene or isopropylbenzene (cumene), ethers such as tetrahydrofuran (THF), diethyl ether, methyl tert-butyl ether or dimethoxyethane (DME), amines such as diisopropylamine, tetramethylethanediamine (TMEDA) or pyridine. Very well-suited solvents are Lewis-base-containing mixtures of hydrocarbons and ethers or amines or both, for example mixtures of toluene and THF, toluene and DME or toluene and TMEDA, where the Lewis base is generally present in an amount of 0.01–50 mol %, preferably 0.1–10 mol %, based on the solvent mixture. Particularly useful "replacement reagents" are carboxylic halides such as acetyl chloride, phenylacetyl chloride, 2-thiophenacetyl chloride, trichloroacetyl chloride, trimethylacetyl chloride, O-acetylmandeloyl chloride, 1,3,5-benzenetricarboxylic chloride, 2,6-pyridinecarboxylic chloride, tert-butylacetyl chloride, chloroacetyl chloride, 4-chlorophenylacetyl chloride, dichloroacetyl chloride, 3-methoxyphenylacetyl chloride, acetyl bromide, bromoacetyl bromide, acetyl fluoride, benzoyl fluoride, which are generally used in the abovementioned solvents or as such. This usually gives the dihalide analogous to the formula III (X=F, Cl, Br, I) or, in the case of partial (half) replacement of the phenolic ligand, a monohalide. A further well-suited replacement method is reaction of the racemic metallocene complexes, preferably those of the formula III, with organoaluminum compounds such as tri-$C_1$–$C_{10}$-alkylaluminum, e.g. trimethylaluminum, triethylaluminum, tri-n-butylaluminum, triisobutylaluminum. This generally gives, on the basis of present knowledge, the organo compound analogous to III (X=organic radical, e.g. $C_1$–$C_{10}$-alkyl such as methyl, ethyl, n-butyl, i-butyl) and, for example, the organoaluminum binaphthoxide. An analogous method can also be used when the ligand $X^1$ in the complex III is two unbridged phenoxide ligands.

In the cleavage reactions, the components are usually used in the stoichiometric ratio regardless of whether a monosubstituted or disubstituted product is to be obtained.

The cleavage reactions generally take place with retention of the stereochemistry of the metallocene complexes, i.e. there is generally no conversion of the racemic form into the meso form of the metallocene complexes. Rather, particularly when using the above-described chlorination methods, the rac-selectivity can be increased while generally retaining the stereochemistry of the starting (bi)phenoxide or starting bisphenoxide complexes.

The process of the present invention makes it possible to obtain the racemic form of metallocene complexes very selectively. Bridged indenyl-type or benzoindenyl-type metallocenes which have a ligand other than hydrogen next to the bridge (namely the 2 position) can be obtained particularly advantageously.

The racemic metal complexes prepared according to the present invention, particularly those of the formula III or their above-described derivatives obtainable, for example, by replacement of the phenoxide ligands, can be used as catalysts or in catalyst systems for the polymerization of olefinically unsaturated compounds such as ethylene, propylene, 1-butene, 1-hexene, 1-octene or styrene. Their use is particularly advantageous in the stereoselective polymerization of prochiral, olefinically unsaturated compounds such as propylene or styrene. Suitable catalysts or catalyst systems in which the racemic metallocene complexes of the present invention can function as "metallocene component" are usually obtained by means of compounds capable of forming metallocenium ions, as described, for example, in EP-A-0 700 935, page 7, line 34 to page 8, line 21 and formulae (IV) and (V). Further compounds capable of forming metallocenium ions are aluminoxanes $(RAlO)_n$ such as methylaluminoxane.

The racemic metallocene complexes prepared according to the present invention, in particular those of the formula III or their above-described derivatives obtainable, for example, by splitting off the phenoxide ligands, can also be used as reagents or as catalysts or in catalyst systems in stereoselective, in particular organic, synthesis. Examples which may be mentioned are stereoselective reductions or stereoselective alkylations of C=C double bonds or C=O or C=N double bonds.

EXAMPLES

Abbreviations:
bpo=1,1'-bi-2-phenoxide
bip=3,3',5,5'-tetra-t-Bu-1,1'-bi-2-phenoxide Examples in which rac-Selectivity is Achieved by Thermal Isomerization Example 1

Preparation of rac-$Me_2Si$(2-Me-ind)$_2$Zr[3,3',5,5'-(t-Bu)$_4$-1,1'-bi-2-phenoxide]

(rac-$Me_2Si$(2-Me-ind)$_2$Zr(bip) (4C)

0.64 g (1.95 mmol) of $Me_2Si$(2-Me-ind)$_2Li_2$ and 1.39 g (1.95 mmol) of $Cl_2$(THF)$_2$Zr(bip) were mixed dry and about 15 ml of a 10:1 mixture of toluene/THF (volume ratio) were added. The reaction mixture was stirred at room temperature for 12 hours. This resulted in formation of an orange solution and a white precipitate (LiCl). The $^1$H-NMR spectrum of the crude mixture indicated an isomer ratio of about 1:1. The reaction mixture was stirred at 80° C. for 5 hours. The $^1$H-NMR spectrum then indicated an rac/meso ratio of about 16:1. The solution was filtered and the solvent mixture was removed in a high vacuum. This gave 1.17 g (74%) of $Me_2Si$(2-Me-ind)$_2$Zr(bip) as a yellow foam which was pure according to NMR spectroscopy and had an rac/meso ratio of 16:1. The yellow foam was taken up in hexane and cooled to −30° C. After one day, filtration gave 0.35 g (22%) of pure racemic $Me_2Si$(2-Me-ind)$_2$Zr(bip) as a microcrystalline yellow powder. $^1$H-NMR spectrum in $C_6D_6$: see Table B. $^{13}$C-NMR spectrum in $C_6D_6$ (25° C., 600 MHz): 161.1, 141.2, 135.3, 134.8, 134.3, 131.8, 130.9, 129.7, 126.0, 126.8, 124.9, 123.3, 121.8, 111.6, 92.4, 34.3, 32.5, 32.1, 31.8, 18.8, 2.55. The mass spectrum (EI-MS/70 eV) showed the molecular ion peak at m/e 812–821 with the typical isotope distribution. Elemental analysis: found: C 73.64%;

H, 7.73%; Zr, 11.06. calculated: C, 73.74%; H, 7.67%; Zr, 11.20%.

TABLE B

1H-NMR shifts for the complex rac-4C (in ppm, C$_6$D$_6$, 25° C., 600 MHz)

| | Assignment[a] |
|---|---|
| 7.60 (d, 2H) $^3$J (8.4 Hz) | C$_9$H$_5$ (H7, H7') |
| 7.49 (d, 2H) $^4$J (2.4 Hz) | C$_6$H$_2$ (H4, H4') |
| 7.26 (d, 2H) $^3$J (8.4 Hz) | C$_9$H$_5$ (H4, H4') |
| 7.18 (d, 2H) $^4$J (2.4 Hz) | C$_6$H$_2$ (H6, H6') |
| 6.85 (dd, 2H) $^3$J (8.4 Hz) $^3$J (7.2 Hz) | C$_9$H$_5$ (H6, H6') |
| 6.77 (dd, 2H) $^3$J (8.4 Hz) $^3$J (7.2 Hz) | C$_9$H$_5$ (H5, H5') |
| 5.83 (s, 2H) | C$_9$H$_5$ (H3, H3') |
| 2.21 (s, 6H) | (2-CH$_3$—C$_9$H$_5$) |
| 1.36, 1.33 (s, 18H) | (CH$_3$)$_3$C |
| 0.80 (s, 6H) | (CH$_3$)$_2$Si |

[a]Assignment by means of the $^1$H-NMR ROESY technique

Example 2

Synthesis of Me$_2$Si(2-Me-ind-4-Ph)$_2$Zr(3,3'5,5'-tetra-$^t$Bu-1,1'-bi-2-phenoxide)

(Me$_2$Si(2-Me-4-Ph-ind)$_2$Zr(bip)

A) Synthesis of ZrCl$_4$(THF)$_2$ 3.1 g (43.0 mmol) of THF were slowly added dropwise to a suspension of 4.99 g (21.41 mmol) of ZrCl$_4$ in 80 ml of toluene at 0° C. (cooling in an ice bath) over a period of 15 minutes. The suspension was warmed to room temperature and stirred for 1 hour.

B) Synthesis of (3,3'5,5'-tetra-$^t$Bu-1,1'-bi-2-phenolato)Li$_2$ 17.0 ml (45.56 mmol) of a 2.68 molar BuLi solution in toluene were slowly added dropwise to a solution of 8.79 g (21.4 mmol) of 3,3'5,5'-tetra-$^t$Bu-1,1'-bi-2-phenol in 120 ml of toluene and 3.1 g (43.0 mmol) of THF at 0° C. (cooling in an ice bath) over a period of 20 minutes. The clear solution was warmed to room temperature and stirred for 1 hour.

C) Synthesis of Cl$_2$Zr(3,3'5,5'-tetra-$^t$Bu-1,1'-bi-2-phenoxide)(THF)$_2$

The dilithium biphenoxide solution from subreaction B) was added under nitrogen by means of a syringe to the ZrCl$_4$(THF)$_2$ suspension from subreaction A). Residues of dilithium biphenoxide solution remaining in the flask were rinsed in using 10 ml of toluene. The suspension was stirred at room temperature for 4 hours.

D) Synthesis of Me$_2$Si(2-Me-4-Ph-ind)$_2$Li$_2$ 16.4 ml (43.95 mmol) of a 2.68 molar BuLi solution in toluene were slowly added dropwise at room temperature to a solution of 9.8 g (20.90 mmol) of Me$_2$Si(2-Me-4-Ph-indH)$_2$ in 110 ml of toluene and 5 g (69.33 mmol) of THF over a period of 20 minutes. The light-yellow suspension was heated to 60° C., stirred for 1 hour and cooled to room temperature.

E) Synthesis of Me$_2$Si(2-Me-4-Ph-ind)$_2$Zr(bip)

The suspension from C) was added under nitrogen by means of a syringe to the Me$_2$Si(2-Me-4-Ph-ind)$_2$Li$_2$ suspension from substep D) at room temperature. After the addition was complete, the suspension became yellow-orange. The reaction mixture was stirred at room temperature for 12 hours. A $^1$H-NMR spectrum of the reaction mixture indicated an rac-meso ratio of about 1:1. The suspension was heated at 85° C. for 9 hours. $^1$H-NMR spectroscopic analysis of the crude mixture indicated an rac-meso ratio of about 15:1, without signs of impurities or decomposition products. The suspension was filtered, the white precipitate was washed with a little toluene and the combined filtrates were evaporated to about ¼ of their volume in a high vacuum. After some days, an orange crystalline precipitate formed and this was isolated by filtration and subsequent drying. 8 g (39.5%) of pure racemic Me$_2$Si(2-Me-4-Ph-ind)$_2$Zr(bip) were obtained. Proceeding in an analogous fashion (multiple crystallization) gave a total of 17.1 g (85%) of pure racemic Me$_2$Si(2-Me-4-Ph-ind)$_2$Zr(bip).

Elemental analysis for Me$_2$Si(2-Me-4-Ph-ind)$_2$Zr(3,3'-5,5'-tetra-t-Bu-1,1'-bi-2-phenoxide) Found: C, 77.0%; H, 7.4%. calculated: C, 77.0%; H, 7.3%. $^1$H-NMR spectrum in C$_6$D$_6$: see Table C.

TABLE C $^1$H-NMR shifts for the complex (in ppm, C$_6$D$_6$ 25° C., 200 MHZ)

| | Assignment |
|---|---|
| 7.78 (d, 2H) | H (aromatic) |
| 7.44 (d, 2H) | C$_6$H$_2$O (bip) |
| 7.34–6.96 (m, 14 H) | H (aromatic) |
| 6.49 (d, 2H) | C$_6$H$_2$O (bip) |
| 6.36 (s, 2H) | C$_5$H |
| 2.27 (s, 6H) | CH$_3$ |
| 1.32 (s, 18H) | C(CH$_3$)$_3$ |
| 1.25 (s, 18H) | C(CH$_3$)$_3$ |
| 0.99 (s, 6H) | Me$_2$Si |

Example 3

Synthesis of Me$_2$Si(2-Me-4-(4-$^t$Bu-Ph-ind)$_2$Zr(3,3'5,5'-tetra-$^t$Bu-1,1'-bi-2-phenoxide)

Me$_2$Si(2-Me-4-(4-$^t$Bu-Ph)-ind)$_2$Zr(bip)

A) Synthesis of ZrCl$_4$(THF)$_2$ 3.8 g (52.7 mmol) of THF were slowly added dropwise to a suspension of 5.45 g (23.38 mmol) of ZrCl$_4$ in 100 ml of toluene at 0° C. (cooling in an ice bath) over a period of 15 minutes. The suspension was warmed to room temperature and stirred for 1 hour.

B) Synthesis of (3,3'5,5'-tetra-$^t$Bu-1,1'-bi-2-phenolato)Li$_2$ 18.3 ml (49.1 mmol) of a 2.68 molar BuLi solution in toluene were slowly added dropwise to a solution of 9.6 g (23.38 mmol) of 3,3'5,5'-tetra-$^t$Bu-1,1'-bi-2-phenol in 130 ml of toluene and 3.8 g (52.7 mmol) of THF at 0° C. (cooling in an ice bath) over a period of 20 minutes. The clear light-yellow solution was warmed to room temperature and stirred for 1 hour.

C) Synthesis of Cl$_2$Zr(3,3'5,5'-tetra-$^t$Bu-1,1'-bi-2-phenoxide)(THF)$_2$

The lithium biphenoxide solution from subreaction B) was added under nitrogen by means of a syringe to the ZrCl$_4$(THF)$_2$ suspension from subreaction A). Residues which remained in the flask were rinsed in using 10 ml of toluene. The suspension was stirred at room temperature for 4 hours.

D) Synthesis of Me2Si(2-Me-4-(4'-$^t$Bu-Ph)-ind)$_2$Li$_2$ 17.5 ml (46.9 mmol) of a 2.68 molar BuLi solution in toluene were slowly added dropwise at room temperature to a solution of 13.0 g (22.38 mmol) of Me$_2$Si(2-Me-4-(4'-$^t$Bu-Ph)-indH)$_2$ in 150 ml of toluene and 6 g (83.20 mmol) of THF over a period of 20 minutes. The light-yellow suspension was heated to 60° C., stirred for 1 hour and cooled to room temperature.

E) Synthesis of Me$_2$Si(2-Me-4-(4'-$^t$Bu-Ph)-ind)$_2$Zr(bip)

The suspension from C) was added under nitrogen by means of a syringe to the Me2Si(2-Me-4-(4'-$^t$Bu-Ph)-ind)$_2$Li$_2$ suspension from substep D) at room temperature. After the addition was complete, the suspension became yellowish. The reaction mixture was stirred at room temperature for 12 hours. A $^1$H-NMR spectrum of the reaction mixture indicated an rac-meso ratio of about 1:2. The suspension was heated at 85° C. for 9 hours. The $^1$H-NMR spectroscopic analysis of the crude mixture indicated an rac-meso ratio of about 15:1 without signs of impurities or decomposition products. The suspension was filtered, the white precipitate was washed with a little toluene and the combined filtrates were evaporated to about ¼ of their volume in a high vacuum. Repeated crystallization at room temperature, filtration and drying gave a total of 21.1 g (88%) of pure racemic Me$_2$Si(2-Me-4-(4'-t-Bu-Ph-ind)$_2$Zr(bip).

Me$_2$Si(2-Me-4-(4'-t-Bu-PH)$_2$Zr(3,3'-5,5'-tetra-t-Bu-1,1'-bi-2-phenoxide)
$^1$H-NMR shifts (in ppm, C$_6$D$_6$ 25° C., 200 MHz)

| | |
|---|---|
| 7.76 (m, 4H) | H$_{arom.}$ |
| 7.76 (m, 4H) | H$_{arom.}$ |
| 7.47 (d, 2H) | C$_6$H$_2$ (biphenol) |
| 7.35–6.95 (m, 10H) | H$_{arom.}$ |
| 6.56 (d, 2H) | C$_6$H$_2$ (biphenol) |
| 6.34 (s, 2H) | C$_5$H |
| 2.26 (s, 6H) | CH$_3$ |
| 1.33 (s, 18H) | (CH$_3$)$_3$C |
| 1.28 (s, 18H) | (CH$_3$)$_3$C |
| 1.27 (s, 18H) | (CH$_3$)$_3$C |
| 0.99 (s, 6H) | Me$_2$Si |

Example in Which rac-Selectivity is Achieved by Addition of Free Radical Sources and Heating (Isomerization)

Example 4

Synthesis of rac-Me$_2$Si(2-Me-benz[e]ind)$_2$Zr(bip) (5C)

0.89 g (2.10 mmol) of Me$_2$Si(2-Me-benz[e]ind)$_2$Li$_2$ and 1.50 g (2.10 mmol) of Cl$_2$(THF)$_2$Zr(bip) were mixed dry and about 15 ml of a 10:1 mixture of toluene/THF (volume ratio) were added. The reaction mixture was stirred at room temperature for 12 hours. This resulted in formation of an orange solution and a white precipitate (LiCl). The $^1$H-NMR spectrum of the crude mixture indicated an isomer ratio of about 1:1. The reaction mixture was filtered. 0.30 g (1.92 mmol) of TEMPO was added to the filtrate at room temperature and the reaction mixture was heated at 75° C. for 1 hour. The $^1$H-NMR spectrum of the crude mixture indicated pure racemic Me$_2$Si(2-Me-benz[e]ind)$_2$Zr(bip). Concentration of the solution by evaporation in a high vacuum and multiple crystallization at room temperature gave a total of 1.6 g (1.76 mmol; 84%) of rac-Me$_2$Si(2-Me-benz[e]ind)$_2$Zr(bip).

$^1$H-NMR spectrum in CDCl$_3$: see Table E. $^{13}$C-NMR spectrum in CDCl$_3$ (25° C., 600 MHz): 158.1, 139.1, 133.3, 133.1, 131.8, 131.6, 130.1, 128.9, 128.2, 127.6, 127.2, 126.4, 125.6, 124.1, 124.0, 121.2, 110.8, 97.3, 35.3, 34.0, 33.1, 31.8, 19.1, 2.9. The mass spectrum (EI-MS/70 eV) displays a molecular ion peak at m/e 906–915 with the typical isotope distribution. Elemental analysis: found: C, 75.99% ; H, 7.09%; Zr, 9.83%. calculated: C, 76.18%; H, 7.27%; Zr, 9.97%.

TABLE E $^1$H-NMR shifts for the complex rac-5C (in ppm, CDCl$_3$, 25° C., 600 MHz)

| | | Assignment[a] |
|---|---|---|
| 7.62 (d, 2H) | $^3$J (8.5 Hz) | C$_{13}$H$_7$ (H8/9, H8'/9') |
| 7.47 (d, 2H) | $^3$J (7.8 Hz) | C$_{13}$H$_7$ (H7, H7') |
| 7.19 (d, 2H) | $^3$J (8.5 Hz) | C$_{13}$H$_7$ (H8/9, H8'/9') |
| 7.11 (d, 2H) | $^4$J (2.5 Hz) | C$_6$H$_2$ (H4/6, H4'/6') |
| 7.10 (dd, 2H) | $^3$J (7.8 Hz) $^3$J (7.3 Hz) | C$_{13}$H$_7$ (H6, H6') |
| 6.95 (dd, 2H) | $^3$J (7.9 Hz) $^3$J (7.3 Hz) | C$_{13}$H$_7$ (H5, H5') |
| 6.65 (d, 2H) | $^3$J (7.9 Hz) | C$_{13}$H$_7$ (H4, H4') |
| 6.34 (s, 2H) | | C$_{13}$H$_7$ (H3, H3') |
| 6.24 (d, 2H) | $^4$J (2.5 Hz) | C$_6$H$_2$ (H4/6, H4'/6') |
| 2.63 (s, 6H) | | (2-CH$_3$—C$_{13}$H$_7$) |
| 1.38 (s, 6H) | | (CH$_3$)$_2$Si |
| 1.28, 1.02 (s, 18H) | | (CH$_3$)$_3$C |

[a]Assignment by means of the $^1$H-NMR ROESY technique

Examples of the Replacement of Phenoxides on Ansa-metallocene Bisphenoxide Complexes Example 5

Preparation of Me$_2$Si(2-Me-benz[e]ind)$_2$ZrCl$_2$ by Reaction of Me$_2$Si(2-Me-benz[e]ind)$_2$Zr(3,5-Me$_2$-OC$_6$H$_3$)$_2$ with CH$_3$COCl 0.63 g (8.02 mmol) of acetyl chloride in 13 g of toluene were added dropwise at room temperature to a solution of 2.8 g (3.74 mmol) of rac-Me$_2$Si(2-Me-benz[e]ind)$_2$Zr(3,5-Me$_2$-OC$_6$H$_3$)$_2$ in 48 g of toluene and 0.6 g (8.3 mmol) of THF. The solution was stirred at room temperature for 2 days. The light-orange solution became increasingly yellow. After some hours, the formation of a light-yellow crystalline precipitate was observed. The $^1$H-NMR spectrum showed, apart from the resonances of 3,5-Me$_2$-phenyl acetate, signals of pure racemic Me$_2$Si(2-Me-benz[e]ind)$_2$ZrCl$_2$. The light-yellow crystalline precipitate was isolated by filtration, washed with a little toluene and dried in a high vacuum. This gave 1.97 g (3.42 mmol) (92%) of pure racemic Me$_2$Si(2-Me-benz[e]ind)$_2$ZrCl$_2$ in analytically pure form.

Preparation of Me$_2$Si(2-Me-benz[e]ind)$_2$Zr(3,5-Me$_2$-OC$_6$H$_3$)Cl by Reaction of Me$_2$Si(2-Me-benz[e]ind)$_2$Zr(3,5-Me$_2$-OC$_6$H$_3$)$_2$ with CH$_3$COCl 0.26 g (3.34 mmol) of acetyl chloride in 10 g of toluene was added dropwise at room temperature to a solution of 2.5 g (3.34 mmol) of rac-Me$_2$Si(2-Me-benz[e]ind)$_2$Zr(3,5-Me$_2$-OC$_6$H$_3$)$_2$ in 60 g of toluene and 0.25 g (3.4 mmol) of THF. The solution was stirred at room temperature for 2 days. The light-orange solution became increasingly yellow. The $^1$H-NMR spectrum showed, apart from the resonances of 3,5-Me$_2$-phenyl acetate, signals of pure racemic Me$_2$Si(2-Me-benz[e]ind)$_2$Zr(3,5-Me$_2$-OC$_6$H$_3$)Cl. The solution was evaporated to about ¼ of its volume in a high vacuum. After some days, a light-yellow crystalline precipitate was formed and this was filtered off, washed with a little toluene and dried in a high vacuum, giving 2.0 g (90%) of pure racemic Me$_2$Si(2-Me-benz[e]ind)$_2$Zr(3,5-Me$_2$-OC$_6$H$_3$)Cl in analytically pure form.

Elemental analysis for Me$_2$Si(Me-benz[e]ind)$_2$ZrCl(3,5-di-Me-phenoxide): found: C, 67.5%; H, 5.3. calculated: C, 68.8%; H, 5.3%.

Me$_2$Si(2-Me-benz[e]ind)$_2$ZrCl(3,5-di-Me-phenoxide)
$^1$H-NMR shifts (in ppm, CDCl$_3$, 25° C., 200 MHz)

| | |
|---|---|
| 7.90 (d, 1H) | $H_{arom.}$ |
| 7.78 (d, 1H) | $H_{arom.}$ |
| 7.70–6.88 (11m, H) | $H_{arom.}$ |
| 6.69 (s, 1H) | $C_5H$ or $C_6H_3$ (4 position of phenoxide) |
| 6.33 (s, 1H) | $C_5H$ or $C_6H_3$ (4 position of phenoxide) |
| 5.81 (s, 2H) | $C_6H_3$ (2,6 positions of phenoxide) |
| 2.29 (s, 3H) | $CH_3$ |
| 2.20 (s, 3H) | $CH_3$ |
| 2.12 (s, 6H) | 3,5-$(CH_3)_2$ (phenoxide) |
| 0.95 (s, 3H) | $Me_2Si$ |
| 0.89 (s, 3H) | $Me_2Si$ |

What is claimed is:

1. A process for preparing racemic metallocene complexes by reacting bridged or unbridged transition metal-aromatic complexes of the formula I

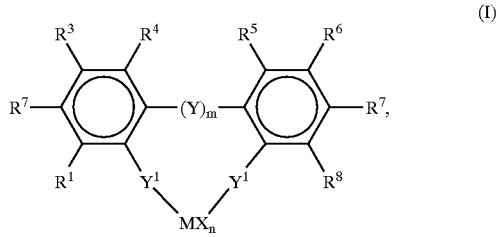

(I)

where the substituents and indices have the following meanings:

M is titanium, zirconium, hafnium, vanadium, niobium, tantalum, chromium, molybdenum, tungsten or an element of transition group III of the Periodic Table or a lanthanide, X are identical or different and are each fluorine, chlorine, bromine, iodine, hydrogen, $C_1$–$C_{10}$alkyl, $C_6$–$C_{15}$-aryl, alkylaryl having from 1 to 10 carbon atoms in the alkyl part and from 6 to 20 carbon atoms in the aryl part, —$OR^{10}$ or —$NR^{10}R^{11}$, n is an integer from 1 to 4, where n corresponds to the valence of M minus 2, $R^1$, $R^8$ are identical or different and are each hydrogen, fluorine, chlorine, bromine, iodine, $C_1$–$C_{20}$-alkyl, 3 to 8-membered cycloalkyl which may in turn bear a $C_1$–$C_{10}$-alkyl group as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $Si(R^9)_3$ where $R^9$ are identical or different and are each $C_1$–$C_{20}$-alkyl, $C_3$–$C_{10}$-cycloalkyl, $C_6$–$C_{15}$-aryl, where the radicals mentioned may be partially or fully substituted by heteroatoms, —$OR^{27}$, —$SR^{27}$, —$N(R^{27})_2$, —$P(R^{27})_2$, where $R^{27}$ are identical or different and are each $C_1$–$C_{10}$-alkyl, $C_6$–$C_{15}$-aryl, $C_3$–$C_{10}$-cycloalkyl, alkylaryl $R^2$ to $R^7$ are identical or different and are each hydrogen, $C_1$–$C_{20}$-alkyl, 3- to 8-membered cycloalkyl which may in turn bear a $C_1$–$C_{10}$-alkyl group as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $Si(R^9)_3$ where $R^9$ are identical or different and are each $C_1$–$C_{20}$-alkyl, $C_3$–$C_{10}$-cycloalkyl, $C_6$–$C_{15}$-aryl, where adjacent radicals $R^2$ to $R^7$ may form saturated, partially saturated or unsaturated cyclic groups having from 4 to 15 carbon atoms, and the radicals mentioned may be fully or partially substituted by heteroatoms, —$OR^{27}$, —$SR^{27}$, —$N(R^{27})_2$, —$P(R^{27})_2$, where $R^{27}$ are identical or different and are each $C_1$–$C_{10}$-alkyl, $C_6$–$C_{15}$-aryl, $C_3$–$C_{10}$-cycloalkyl, alkylaryl $R^{10}$, $R^{11}$ are each $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical, Y, $Y^1$ are identical or different and are each

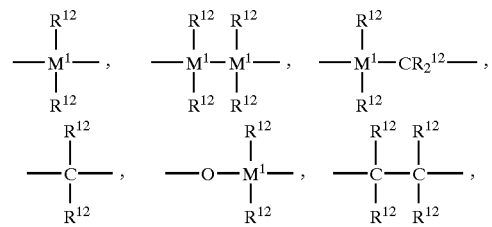

=$BR^{12}$, =$AlR^{12}$, —Ge—, —Sn—, —O—, —S—, =SO, =$SO_2$, =$NR^{12}$, =CO, =$PR^{12}$ or =$P(O)R^{12}$, where $R^{12}$ are identical or different and are each hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl, $C_7$–$C_{40}$-alkylaryl, or two radicals $R^{12}$ together with the atoms connecting them form a ring, $M^1$ is silicon, germanium or tin and m is 0, 1, 2, 3, or Y is nonbridging and represents two radicals R' and R", where R' and R" are identical or different and are each hydrogen, fluorine, chlorine, bromine, iodine, $C_1$–$C_{20}$-alkyl, 3- to 8-membered cycloalkyl which may in turn bear a $C_1$–$C_{10}$-alkyl group as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $Si(R^9)_3$ where $R^9$ are identical or different and are each $C_1$–$C_{20}$-alkyl, $C_3$–$C_{10}$-cycloalkyl, $C_6$–$C_{15}$-aryl or together with adjacent radicals or $R^5$ form saturated, partially saturated or unsaturated cyclic groups having from 4 to 15 carbon atoms, and the radicals mentioned may be fully or partially substituted by heteroatoms, —$OR^{27}$, —$SR^{27}$, —$N(R^{27})_2$, —$P(R^{27})_2$, where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$ where $R^{28}$ are identical or different and are each $C_1$–$C_{10}$, $C_6$–$C_{15}$-aryl, $C_3$–$C_{10}$-cycloalkyl, alkylaryl with cyclopentadienyl derivatives of alkali metals or alkaline earth metals, heating the reaction mixture obtained in this way to from 75 to 180° C. with or without addition of free radicals or free radical formers, and, optionally, subsequently replacing the bridged phenolic ligand or the two unbridged phenolic ligands to form the monosubstitution or disubstitution product.

2. A process as claimed in claim 1, wherein $R^1$ and $R^8$ in formula I are bulky substituents.

3. A process as claimed in claim 1, wherein m in formula I is 0.

4. A process as claimed in claim 1, wherein $Y^1$ are identical and are each oxygen.

5. A process as claimed in claim 1, wherein cyclopentadienyl derivatives of magnesium or lithium are used.

6. A process for preparing racemic metallocene complexes by reacting bridged or unbridged transition metal-aromatic complexes of the formula I

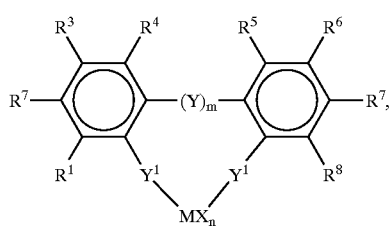

where the substituents and indices have the following meanings:

M is titanium, zirconium, hafnium, vanadium, niobium, tantalum, chromium, molybdenum, tungsten or an element of transition group III of the Periodic Table or a lanthanide, X are identical or different and are each fluorine, chlorine, bromine, iodine, hydrogen, $C_1$–$C_{10}$-alkyl, $C_6$–$C_{15}$-aryl, alkylaryl having from 1 to 10 carbon atoms in the alkyl part and from 6 to 20 carbon atoms in the aryl part, —$OR^{10}$ or —$NR^{10}R^{11}$, n is an integer from 1 to 4, where n corresponds to the valence of M minus 2, $R^1$, $R^3$, $R^6$, $R^8$ are each hydrogen;

$R^2$, $R^4$, $R^5$, $R^7$ are identical or different and are each $C_1$–$C_{20}$-alkyl, 3- to 8-membered cycloalkyl which may in turn bear a $C_1$–$C_{10}$-alkyl group as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, $Si(R^9)_3$ where $R^9$ are identical or different and are each $C_1$–$C_{20}$-alkyl, $C_3$–$C_{10}$-cycloalkyl, $C_6$–$C_{15}$-aryl, where adjacent radicals $R^2$ to $R^7$ may form saturated, partially saturated or unsaturated cyclic groups having from 4 to 15 carbon atoms, and the radicals mentioned may be fully or partially substituted by heteroatoms, —$OR^{27}$, —$SR^{27}$, —$N(R^{27})_2$, —$P(R^{27})_2$, where $R^{27}$ are identical or different and are each $C_1$–$C_{10}$-alkyl, $C_6$–$C_{15}$-aryl, $C_3$–$C_{10}$-cycloalkyl, alkylaryl $R^{10}$, $R^{11}$ are each $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical, $Y^1$ are identical or different and are each

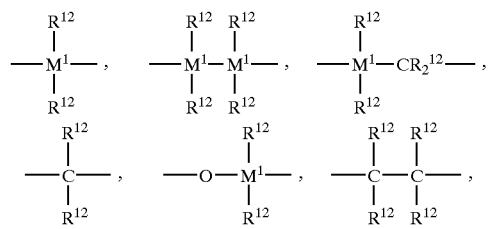

=$BR^2$, =$AlR^{12}$, —Ge—, —Sn—, —O—, —O—, =SO, =$SO_2$,

=$NR^{12}$, =CO, =$PR^{12}$ or =$P(O)R^{12}$, where $R^{12}$ are identical or different and are each hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl, $C_7$–$C_{40}$-alkylaryl, or two radicals $R^{12}$ together with the atoms connecting them form a ring, $M^1$ is silicon, germanium or tin and m is 1, and Y is nonbridging and represents two radicals R' and R", where R' and R" are each hydrogen;

with cyclopentadienyl derivatives of alkali metals or alkaline earth metals, heating the reaction mixture obtained in this way to from 75 to 180° C., with or without addition of free radicals or free radical formers, and, optionally, subsequently replacing the bridged phenolic ligand or the two unbridged phenolic ligands to form the monosubstitution or disubstitution product.

7. A racemic metallocene complex prepared by the process of claim 6.

8. Racemic $Me_2Si(2$-Me-benz[e]ind$)_2Zr(3,5$-$Me_2$-$OC_6H_3)_2$.

9. A process for the stereoselective polymerization of olefinically unsaturated compounds where the catalyst, or a constituent of the catalyst, is the metallocene complex of claim 7.

10. A process as claimed in claim 6, wherein $Y_1$ are identical and are each oxygen.

11. A process as claimed in claim 6, wherein cyclopentadienyl derivatives of magnesium or lithium are used.

* * * * *

UNITED STATES PATENT AND TRADEMARK OFFICE
CERTIFICATE OF CORRECTION

PATENT NO. : 6,992,204 B2
APPLICATION NO. : 10/312359
DATED : January 31, 2006
INVENTOR(S) : Damrau et al.

It is certified that error appears in the above-identified patent and that said Letters Patent is hereby corrected as shown below:

In Claim 1, column 26, lines 51-52, please delete:
"or together with adjacent radicals or $R^5$ form saturated" and substitute therefore:
-- or together with adjacent radicals $R^4$ or $R^5$ form saturated --.

In Claim 6, column 27, beginning at line 14, please replace the formula with the formula listed below:

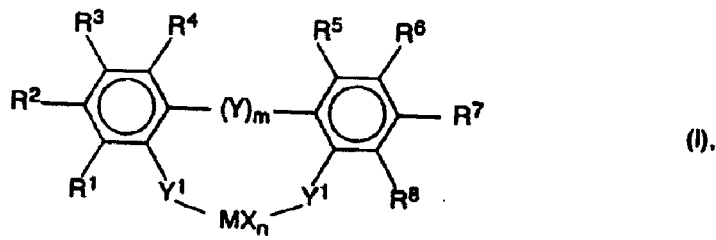

(I).

In Claim 6, column 28, line 18, please delete:
"=$BR^2$,=$AIR^{12}$ -Ge-, -Sn-, -O-, -O-," and substitute therefore:
-- =$BR^2$,=$AIR^{12}$, -Ge-, -Sn-, -O-, -S-, --.

Signed and Sealed this

Third Day of October, 2006

JON W. DUDAS
*Director of the United States Patent and Trademark Office*